(12) United States Patent
Zwanenburg et al.

(10) Patent No.: US 10,444,188 B2
(45) Date of Patent: Oct. 15, 2019

(54) MONITORING PIPE CONDITIONS

(71) Applicant: Schlumberger Technology Corporation, Sugar Land, TX (US)

(72) Inventors: Mirjam Zwanenburg, Amsterdam (NL); David P. Smith, Anchorage, AK (US); Zhanke Liu, Sugar Land, TX (US); Michelle Torregrossa, Houston, TX (US); Liam Zsolt, Anchorage, AK (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/024,314

(22) PCT Filed: Oct. 1, 2013

(86) PCT No.: PCT/US2013/062839
§ 371 (c)(1),
(2) Date: Mar. 23, 2016

(87) PCT Pub. No.: WO2015/050526
PCT Pub. Date: Apr. 9, 2015

(65) Prior Publication Data
US 2016/0231280 A1   Aug. 11, 2016

(51) Int. Cl.
*G01N 27/87* (2006.01)
*E21B 47/00* (2012.01)
*G01N 27/83* (2006.01)

(52) U.S. Cl.
CPC .............. *G01N 27/87* (2013.01); *E21B 47/00* (2013.01); *G01N 27/83* (2013.01)

(58) Field of Classification Search
CPC ... E21B 47/0905; E21B 47/082; G01N 27/83; G01N 27/82; G01N 27/902; G01V 3/26
(Continued)

(56) References Cited

U.S. PATENT DOCUMENTS 5,914,596 A * 6/1999 Weinbaum ........... G01N 29/225
324/228
6,321,596 B1 * 11/2001 Newman ................. E21B 19/22
73/152.45
(Continued)

FOREIGN PATENT DOCUMENTS

WO     2012174057 A1     12/2012
WO     2015050526 A1      4/2015

OTHER PUBLICATIONS

International Search Report and the Written Opinion for International Application No. PCT/US2013/062839 dated Jul. 10, 2014.

*Primary Examiner* — Christopher P McAndrew

(57) ABSTRACT

A technique facilitates monitoring of pipe, such as coiled tubing. The monitoring may be used to detect conditions which occur within the pipe itself or in components employed along an interior of the pipe. A magnetic sensor system is positioned along an exterior of the pipe, e.g. coiled tubing. During relative movement between the pipe and the magnetic sensor system, the magnetic sensor system monitors for the condition, e.g. change/abnormality, of interest. In some applications, the magnetic sensor system is used to monitor changes in a physical property of the pipe, and/or a component within the pipe, during a succession of operations employing the pipe.

12 Claims, 6 Drawing Sheets

(58) Field of Classification Search
USPC .......................................................... 324/221
See application file for complete search history.

(56) References Cited

U.S. PATENT DOCUMENTS

| | | | |
|---|---|---|---|
| 6,450,259 B1 * | 9/2002 | Song | E21B 47/022 |
| | | | 166/255.1 |
| 6,720,764 B2 | 4/2004 | Relton et al. | |
| 7,258,296 B2 * | 8/2007 | Smith | B21C 47/143 |
| | | | 242/361 |
| 7,458,267 B2 * | 12/2008 | McCoy | G01N 29/44 |
| | | | 73/587 |
| 2004/0118960 A1 * | 6/2004 | Smith | B21C 47/143 |
| | | | 242/361 |
| 2007/0165487 A1 * | 7/2007 | Nutt | E21B 31/18 |
| | | | 367/25 |
| 2008/0042645 A1 | 2/2008 | Kaack et al. | |
| 2013/0187641 A1 * | 7/2013 | Singer | G01N 27/82 |
| | | | 324/220 |
| 2013/0284434 A1 * | 10/2013 | Marvel | E21B 47/04 |
| | | | 166/255.1 |

* cited by examiner

MONITORING PIPE CONDITIONS

BACKGROUND

Coiled tubing is used in a variety of well applications. The coiled tubing may be deployed downhole into a wellbore via a coiled tubing reel and a coiled tubing injector for performing intervention operations and/or other types of well servicing operations. During use, conditions, e.g. abnormalities, may occur in the coiled tubing and the severity of these abnormalities may increase as the coiled tubing is used repeatedly for subsequent well related operations. Examples of these conditions in the coiled tubing include bias weld spiraling and stretching of the coiled tubing at various locations along the coiled tubing.

SUMMARY

In general, a technique is provided for monitoring pipe, such as coiled tubing. The monitoring may be employed for conditions which occur within the pipe itself or in components employed along an interior of the pipe. A magnetic sensor system is positioned along an exterior of the pipe, e.g. coiled tubing. During relative movement between the pipe and the magnetic sensor system, the magnetic sensor system monitors for the condition, e.g. change/abnormality, of interest. In some applications, the magnetic sensor system is used to monitor changes in a physical property of the pipe, and/or a component within the pipe, during a succession of operations employing the pipe.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
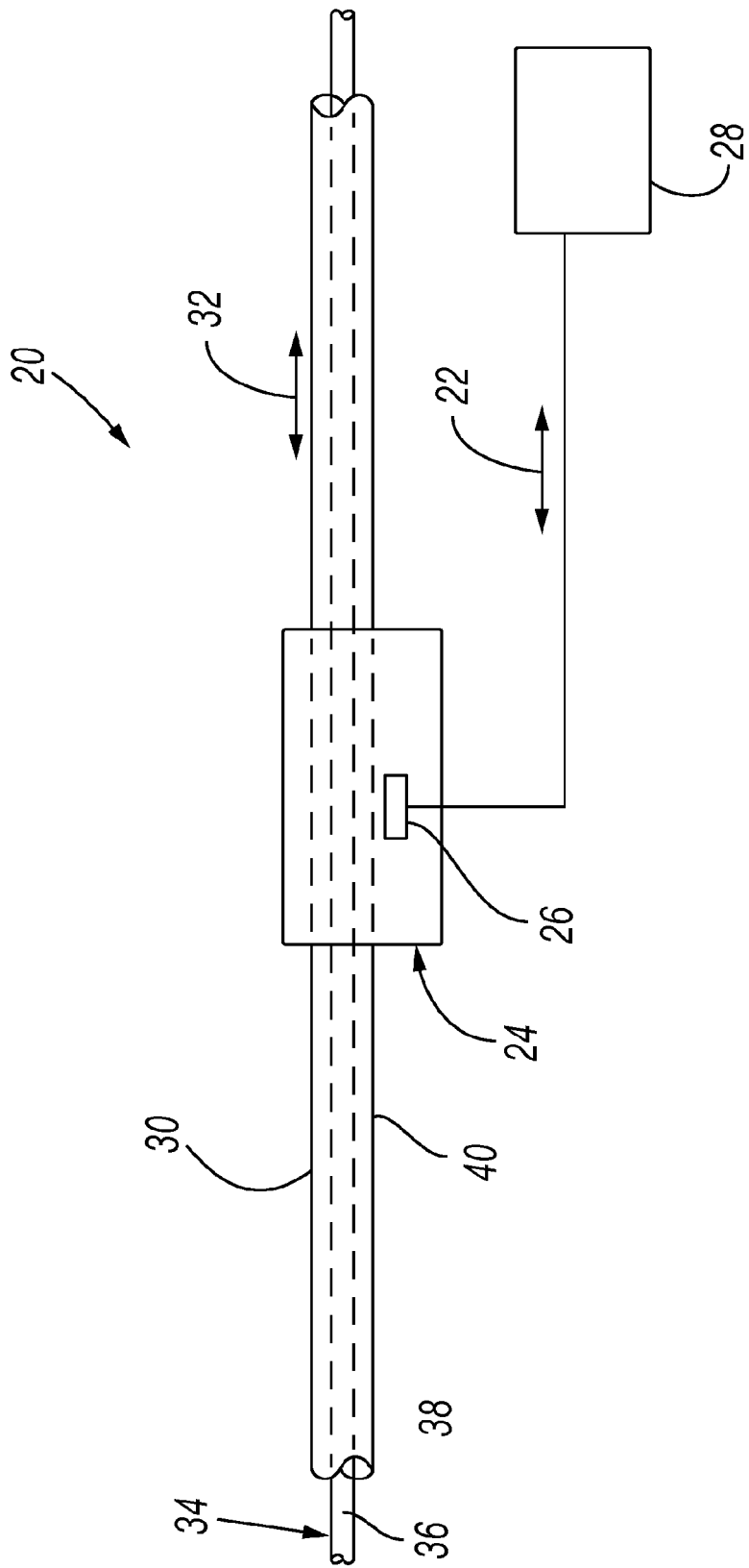
FIG. 1 is a schematic illustration of an example of a pipe monitoring system, according to an embodiment of the disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a system and methodology for monitoring conditions related to a pipe. The conditions may comprise changes/abnormalities in the pipe itself and/or in an internal component disposed within the pipe. By way of example, a magnetic sensing system may be positioned along an exterior of the pipe for monitoring magnetic lines indicative of a given condition as relative longitudinal movement occurs between the pipe and the magnetic sensing system. The technique may be employed for well and non-well related applications. In certain well applications, the magnetic sensing system may be used along coiled tubing to monitor conditions of the coiled tubing and/or of components within the coiled tubing as the coiled tubing is spooled or unspooled with respect to a wellbore.

In an embodiment, a magnetic sensor system is positioned along an exterior of the pipe, e.g. coiled tubing. By way of example, the magnetic sensor system may comprise a magnetic flux leakage sensor oriented to detect specific conditions in real time. During relative movement between the pipe and the magnetic sensor system, the magnetic sensor monitors a magnetic flux leakage signal to detect the condition, e.g. changes/abnormalities, of interest. Data on the condition is relayed to a suitable processing system, such as a computer-based system. As the coiled tubing or other pipe is employed in subsequent operations or jobs, progression of the condition may be monitored and tracked from one operation to the next. In some applications, the magnetic sensor system is used to monitor changes in a physical property of the pipe. The magnetic sensor system also may be used to monitor for conditions of a component, e.g. cable, within the pipe.

Examples of conditions monitored by the magnetic sensing system comprise changes, such as detrimental changes in a physical property of the pipe. In coiled tubing applications, the detrimental changes may comprise pipe stretching along the coiled tubing or at specific regions along the coiled tubing. The detrimental changes also may comprise seam weld spiraling. As the coiled tubing is unspooled and spooled repeatedly for subsequent operations, progression of the detrimental changes can occur. The magnetic monitoring system enables tracking of the progression. In some applications, the magnetic sensor system also may be used to monitor conditions of an internal component within the pipe. For example, if cable is deployed along an interior of the coiled tubing or other pipe, the magnetic sensor may be used to detect areas of slack in the cable. This data enhances the ability of an operator to manage cable slack. It should be noted, however, the magnetic monitoring system may be employed with a variety of pipes for monitoring many types of abnormalities and other conditions.

Referring generally to FIG. 1, an embodiment of a system 20 employing a pipe monitoring system 22 is illustrated. In this example, pipe monitoring system 22 comprises a magnetic sensor system 24 having a magnetic sensor or sensors 26. The pipe monitoring system 22 also comprises a suitable data processing system 28. Data from the magnetic sensor system 24 and magnetic sensor 26 is provided to the processing system 28, which may be in the form of a computer-based processing system. By way of example, the magnetic sensor or sensors 26 may comprise magnetic flux leakage sensors designed and oriented to monitor a magnetic flux leakage signal in real time.

As illustrated, the sensor 26 is mounted along an exterior of a pipe 30. By way of example, pipe 30 may comprise coiled tubing or a variety of other types of pipe. Relative motion is created between pipe 30 and magnetic sensor system 24, as indicated by arrow 32. For example, pipe 30 may be moved linearly in a longitudinal direction past magnetic sensor 26 in either direction indicated by arrow 32. In some applications, however, the magnetic sensor 26 and magnetic sensor system 24 could be moved relative to pipe 30. In other applications, both the magnetic sensor system 24 and the pipe 30 could be moved to cause the relative motion.

The magnetic sensor 26, e.g. a magnetic flux leakage sensor, is designed to detect conditions, e.g. changes/abnormalities, in the pipe 30 during the relative movement between pipe 30 and magnetic sensor system 24. Data on these conditions may be supplied by magnetic sensor 26 to the data processing system 28. When pipe 30 is used in a plurality of operations or jobs, the data processing system 28 may be used to track data on the condition to determine any progression of the condition from one operation to the next. In some applications, the magnetic sensor system 24 and magnetic sensor 26 may be used to monitor conditions of an internal component 34 disposed within the pipe 30. By way of example, internal component 34 may comprise a cable 36 routed along an interior 38 of pipe 30. In this latter example, magnetic sensor 26 may be used to determine regions of slack within the cable 36 or to determine other internal component conditions.

The magnetic sensor system 24 may be employed to determine and monitor conditions of the pipe 30, of the internal component 34, or of both the pipe 30 and the internal component 34. Because sensor 26 is a magnetic sensor, the sensor 26 may be located along an exterior 40 of pipe 30 while still providing valuable information on conditions occurring in the pipe 30 and/or conditions related to the internal component 34. When changes in the condition occur from operation to operation, data processing system 28 analyzes the real time data from each operation to compare the changes and to determine condition progression. Continued progression of a condition may indicate to an operator that the pipe 30 and/or internal component 34 should be repaired or replaced.

Figure 2:
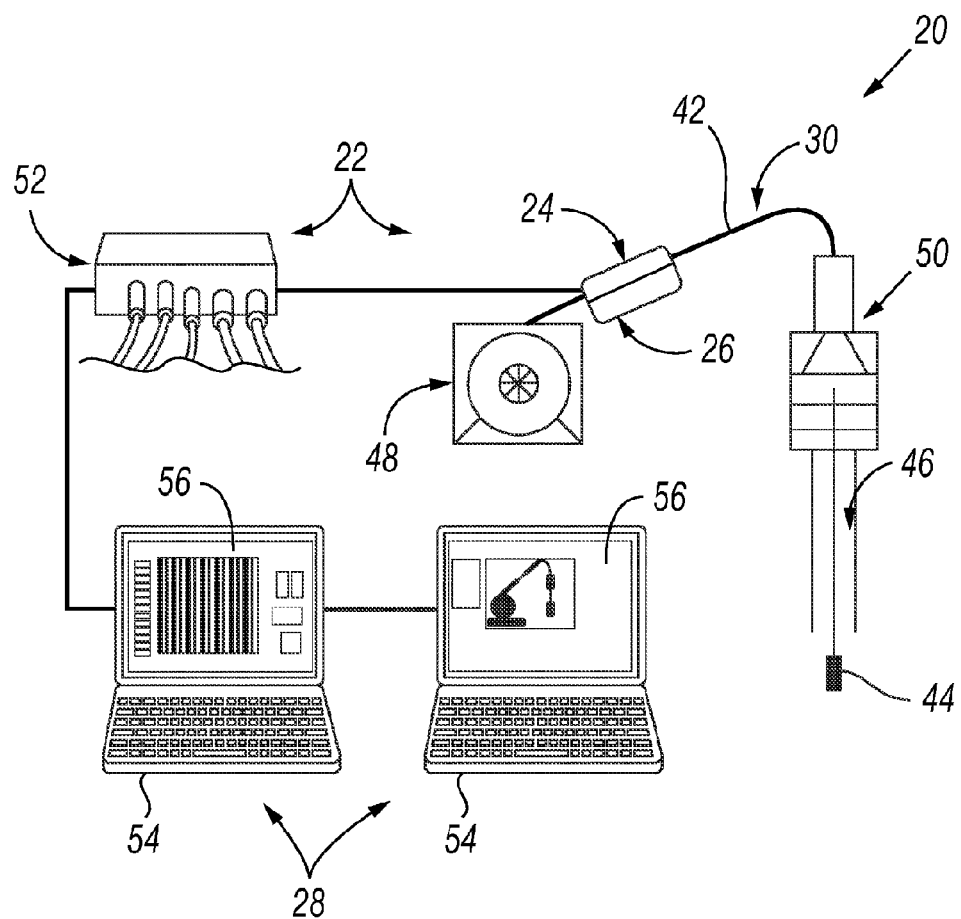
FIG. 2 is a schematic illustration of one of many examples of a well application utilizing a coiled tubing monitoring system, according to an embodiment of the disclosure.

Referring generally to FIG. 2, a well related embodiment of system 20 is illustrated. However, this embodiment is representative and many other types of embodiments may be designed to utilize a magnetic sensor system able to monitor magnetic lines for detection of conditions, e.g. abnormalities, in the coiled tubing or other pipe. In the embodiment illustrated, pipe 30 is in the form of coiled tubing 42. The coiled tubing 42 may be used to deploy a variety of well tools 44 downhole into a wellbore 46. For example, the coiled tubing 42 may be used in intervention operations or other types of well service operations. Often, the coiled tubing 42 is used repeatedly from one operation to the next, e.g. from one intervention operation to the next, at an individual well or at a plurality of different wells.

The coiled tubing 42 may be unspooled from a coiled tubing reel 48 and deployed downhole into wellbore 46 via a coiled tubing injector 50. Similarly, the coiled tubing reel 48 may be operated to spool the coiled tubing 42 and to withdraw the coiled tubing 42 and well tool 44 from wellbore 46. In the application illustrated, pipe monitoring system 22 is constructed with magnetic sensor system 24 positioned between coiled tubing reel 48 and coiled tubing injector 50. The magnetic sensor system 24 supports magnetic sensor 26 at a desired position and orientation external to coiled tubing 42. As the coiled tubing 42 is unspooled or spooled, relative movement occurs between the coiled tubing 42 and the external magnetic sensor 26 as the coiled tubing 42 is moved past magnetic sensor system 24. The external location of magnetic sensor 26 facilitates pumping of fluid through the interior 38 of the pipe 30/coiled tubing 42 (or other operational procedures) while using sensor 26 in real time to detect and monitor changes with respect to a given condition.

In the example illustrated in FIG. 2, the magnetic sensor system 24 may comprise a variety of hardware 52 to facilitate operation of magnetic sensor 26 and transmission of data from sensor 26. The type of hardware 52 depends on the environment, the conditions being sensed, and the type of sensor 26. In some applications, for example, sensor 26 comprises a magnetic flux leakage sensor which is useful for determining conditions of the pipe 30, e.g. coiled tubing 42, and/or of internal components 34. The magnetic flux leakage sensor system 24 establishes a magnetic field through the pipe 30 and the magnetic lines are detected via sensor 26. The monitored flux leakage is constant if the pipe integrity is constant. However, if the wall thickness of the pipe changes (and/or other changes/abnormalities in the pipe occur), a change in the flux leakage results and this change is detected by sensor 26. The same approach may be used to monitor for changes in conditions of the internal component 34. Hardware 52 is designed to transfer the data from magnetic sensor 26 to data processing system 28.

Data processing system 28 may have a variety of forms and may be located on-site, at a remote location, or with components on-site and at remote locations. In the illustrated example, the data processing system 28 is a computer-based processing system which utilizes one or more microprocessors or other suitable processors for evaluating data from the one or more magnetic sensors 26. By way of example, the data processing system 28 may comprise a plurality of computers 54 having graphical user interfaces 56 for outputting data related to conditions of the pipe 30 and/or internal component 34 as well as changes in those conditions from one operation or operation to another. It should be noted that well-related applications utilizing coiled tubing 42 commonly use internal cable or other internal components 34 which may be monitored by magnetic sensor system 24.

The graphical user interfaces 56 may be employed to display data on the progressive changes in a condition of the coiled tubing 42 as the coiled tubing 42 is used at a given initial well operation and then at a plurality of subsequent well operations. In an operational example, the magnetic sensor system 24 is positioned along an exterior of the pipe 30, e.g. coiled tubing 42. Relative movement between the pipe 30 and the magnetic sensor system 24 is then caused. For example, coiled tubing reel 48 may be operated to unspool coiled tubing 42 through magnetic sensor system 24 and past magnetic sensor 26 as the coiled tubing is delivered downhole into wellbore 46 for a given operation. Similarly, magnetic sensor 26 may be operated to detect and monitor for conditions in real time as the coiled tubing 42 is spooled by coiled tubing reel 48 and as the well tool 44 is pulled out of hole. The data from magnetic sensor 26 is recorded and processed via processing system 28.

The procedure of positioning the sensor 26 along an exterior of the pipe 30 and causing relative movement between the sensor 26 and the pipe 30 is then repeated at a plurality of subsequent operations. In the coiled tubing example, the plurality of subsequent operations may be a plurality of subsequent intervention operations. The magnetic sensor system 24 enables monitoring of changes in a condition, e.g. a physical property, of the pipe during the sequential operations in which pipe 30 is employed. In coiled tubing operations, the relative movement and monitoring may occur as the coiled tubing is unspooled, spooled, or both.

By way of example, the pipe monitoring system 22 may be employed to record detailed electronic measurements of the position geometry as well as internal and external changes/abnormalities of the pipe 30 in real time as the pipe 30 moves through magnetic sensor system 24, or vice versa. If sensor 26 comprises a magnetic flux leakage sensor, measurements of a magnetic flux signal can be used to find conditions, e.g. changes/abnormalities, in the pipe 30 and/or internal component 34.

Detection of the magnetic flux signal by sensor 26 may be used for slack management of internal cables 36 by detecting slack in the cable 36 within pipe 30 in real-time. The magnetic sensor 26 is able to detect a distinct signature indicative of excessive cable inside the pipe 30. Additionally, magnetic sensor 26 and magnetic sensor system 24 may be used to detect a magnetic flux leakage signal indicative of pipe stretching. Coiled tubing can be stretched during operations but it is difficult to know the location and extent of the stretching on a operation to operation basis. However, the magnetic flux leakage signal can be used to detect the regions of pipe stretching and to monitor changes in this condition from one coiled tubing operation to the next. Similarly, the magnetic flux leakage signal detected by magnetic sensor 26 may be used to determine seam or bias weld spiraling in the coiled tubing. Similar to the tracking of other conditions, changes in the weld spiraling can be detected by magnetic sensor 26 and tracked via data processing system 28 from one operation or operation to the next in which the pipe 30, e.g. coiled tubing 42, is employed. Tracking these conditions is helpful in monitoring fatigue and other detrimental conditions of pipe 30 and/or internal component 34 as the same pipe 30 is used in a plurality of different, sequential operations. Slack management of internal cables 36 may be critical and may be difficult. In an embodiment, an active slack management method is provided. Systems, such as the system 20 shown in FIG. 2, are sensitive to abnormalities in ferromagnetic materials, such as iron, cobalt, and nickel. However, some cables and/or coils (such as fiber optic tethers or the like) contains primarily Inconel (a non-ferromagnetic material with a permeability similar to air), which are usually invisible or otherwise not detectable to such magnetic systems. In other embodiments of cables and/or coils formed from ferrous materials, if the ferrous material metal distribution in the tubing axis direction is uniform, such cables and/or coils may not generate a signal spikes in the system 20. In an embodiment, such cables and/or coils may be made more visible and tractable by tagging the cables or coils using ferromagnetic materials or active magnetic sources. In an embodiment, the cable and/or coil is tagged with a fixed known distance, for example, every 500 ft, or every 1000 ft, etc. By measuring the distance between successive tags and comparing the measured distance to the original distance, one can determine if there is enough (but not too much) slack left for the cable and/or coil inside the coiled tubing. Such cable or coil tagging may be performed at the time the cable or coil is manufactured.

Figure 3:
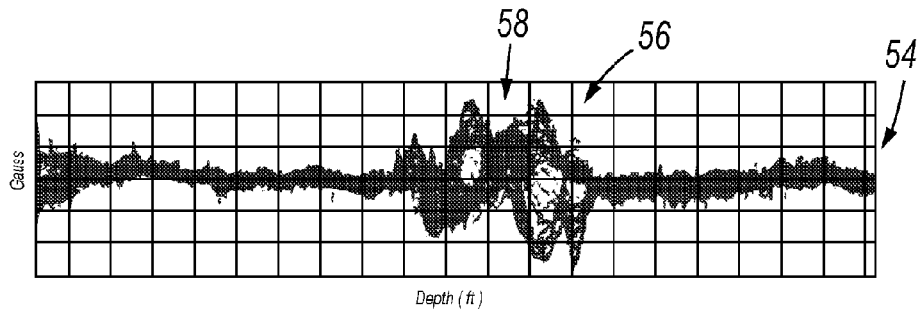
FIG. 3 is a graphical representation of data output by the monitoring system indicating conditions of a component within a pipe, according to an embodiment of the disclosure.
Figure 4:
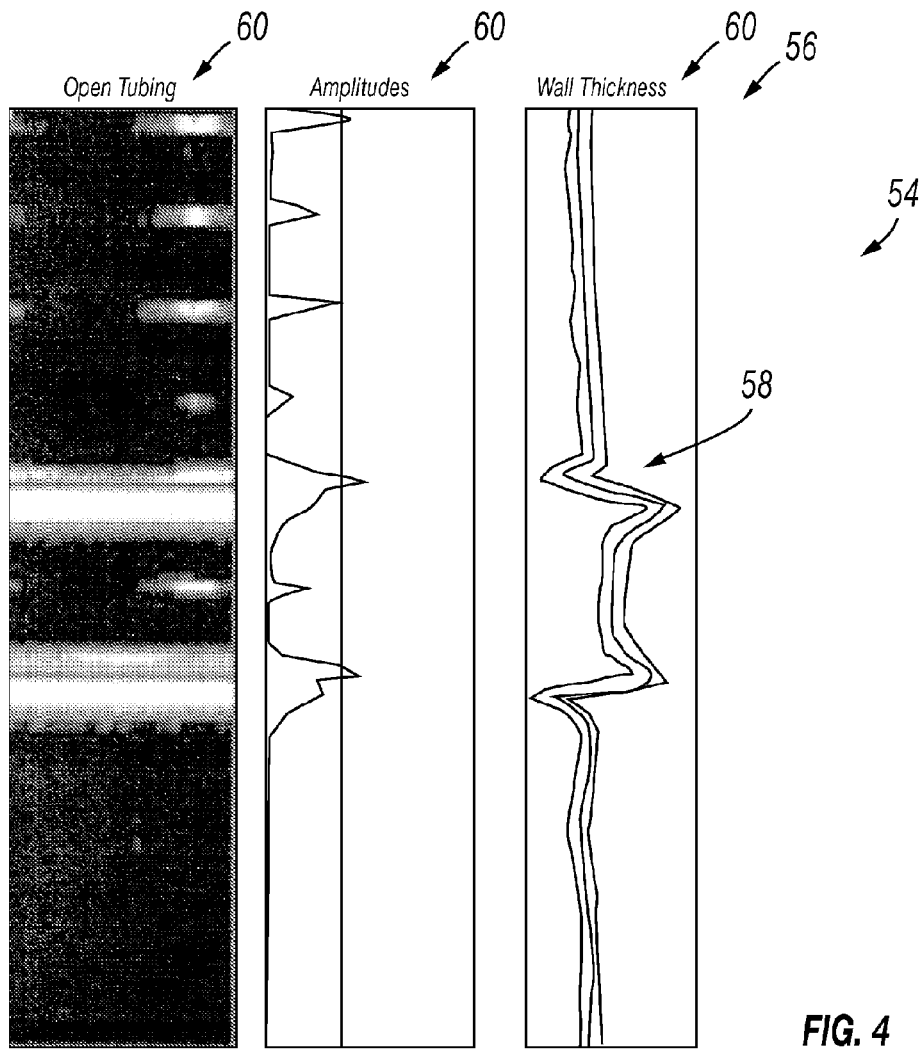
FIG. 4 is another graphical representation of data output by the monitoring system indicating conditions of a component within a pipe, according to an embodiment of the disclosure.

Depending on the condition or conditions being monitored by magnetic sensor system 24, data indicative of the condition may be output in several different forms. By way of example, data on the monitored condition may be output for individual operations and for a plurality of sequential operations via one or more graphical user interfaces 56. Referring to FIG. 3, for example, data related to the monitoring of internal component 34 is output via graphical user interface 56. In this particular example, magnetic sensor 26 is a magnetic flux leakage sensor employed to monitor slack of cable 36 disposed along interior 38 of coiled tubing 42. As illustrated, the data from magnetic sensor 26 provides a signature 58 indicative of cable slack at a particular region along the coiled tubing 42. The regions tending to accumulate cable slack can be monitored for a given operation or over a plurality of operations to gain knowledge of specific pipe regions which tend to accumulate excessive cable slack. This knowledge can be used in implementing suitable cable slack management programs. The position of the cable slack (or other change/abnormality in internal component 34 or coiled tubing 42) is readily determined by tracking the length of coiled tubing unspooled or spooled. As indicated by the graphical user interface 56 of FIG. 4, individual sensors 26 or a plurality of sensors 26 may be employed to monitor a plurality of channels 60 related to individual or plural conditions of the pipe 30 and/or internal component 34. The condition may again be indicated by signatures 58 displayed with respect to certain channels 60.

Figure 5:
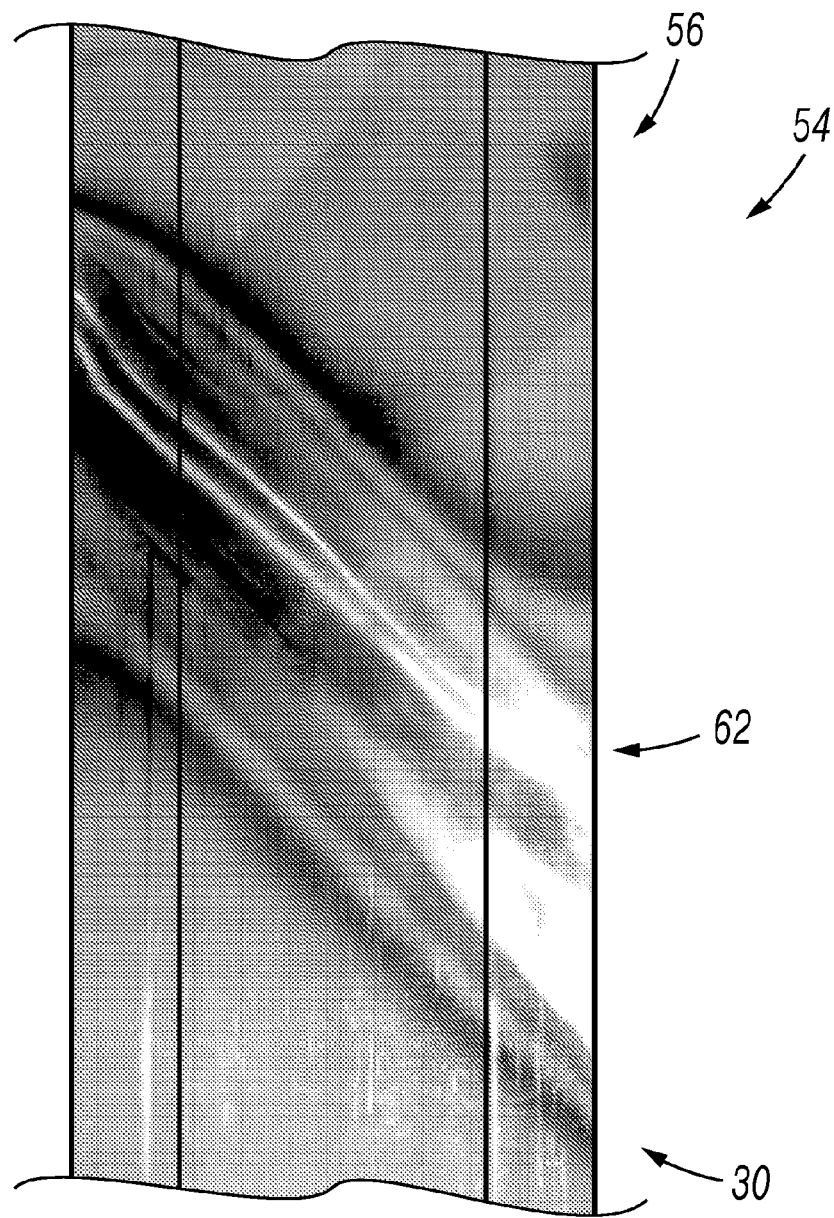
FIG. 5 is an illustration of a steel material with a condition, e.g. bias weld, that can change during use of the material, according to an embodiment of the disclosure.
Figure 6:
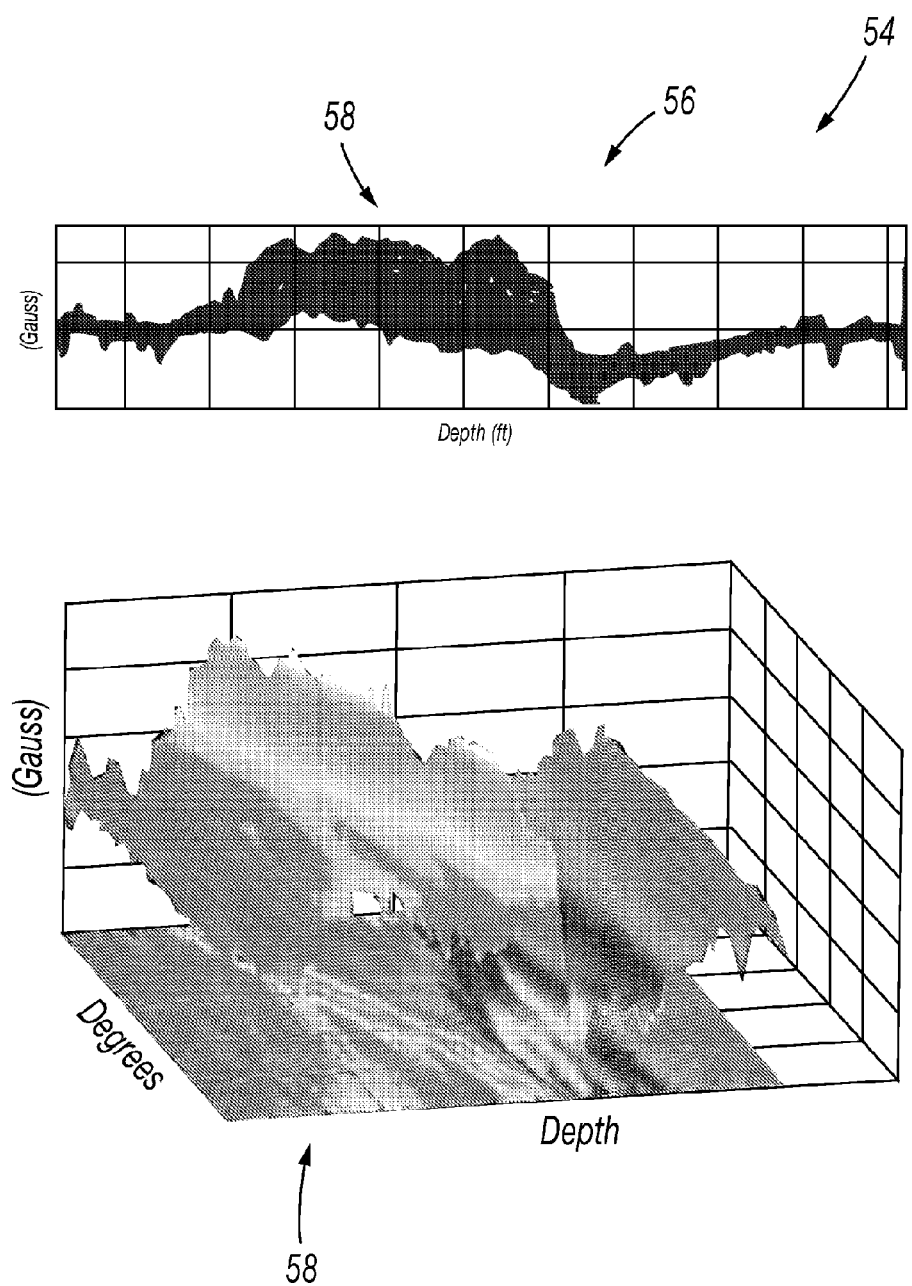
FIG. 6 is a graphical representation of data output by the monitoring system indicating a progressively changing condition, e.g. changing bias weld, within a pipe, according to an embodiment of the disclosure.

In another example, the magnetic sensor system 24 and magnetic sensor 26 may be used to monitor magnetic flux leakage signals indicative of pipe stretch or other conditions. In FIG. 5, the magnetic sensor system 24 has been employed to monitor a condition (bias weld) in a steel material, e.g. steel coiled tubing. The data from magnetic flux leakage sensor 26 may be output via graphical user interface 56 to show indications of, for example, pipe stretch via changes to a bias weld 62 within the pipe 30, e.g. coiled tubing 42. As further illustrated in FIG. 6, the pipe stretch has a specific signature 58 which is easily identified. The pipe stretch data providing signature 58 can be accumulated via processing system 28 for each operation in which the coiled tubing 42 (or other pipe 30) is employed. This accumulation of data from a given operation and from the plurality of subsequent operations enables tracking of pipe fatigue or wear as the same coiled tubing 42 is used repeatedly from one operation to the next. The progression of pipe stretch can be output graphically, or in some other form, and displayed via graphical user interface 56 for the plurality of operations.

Figure 7:
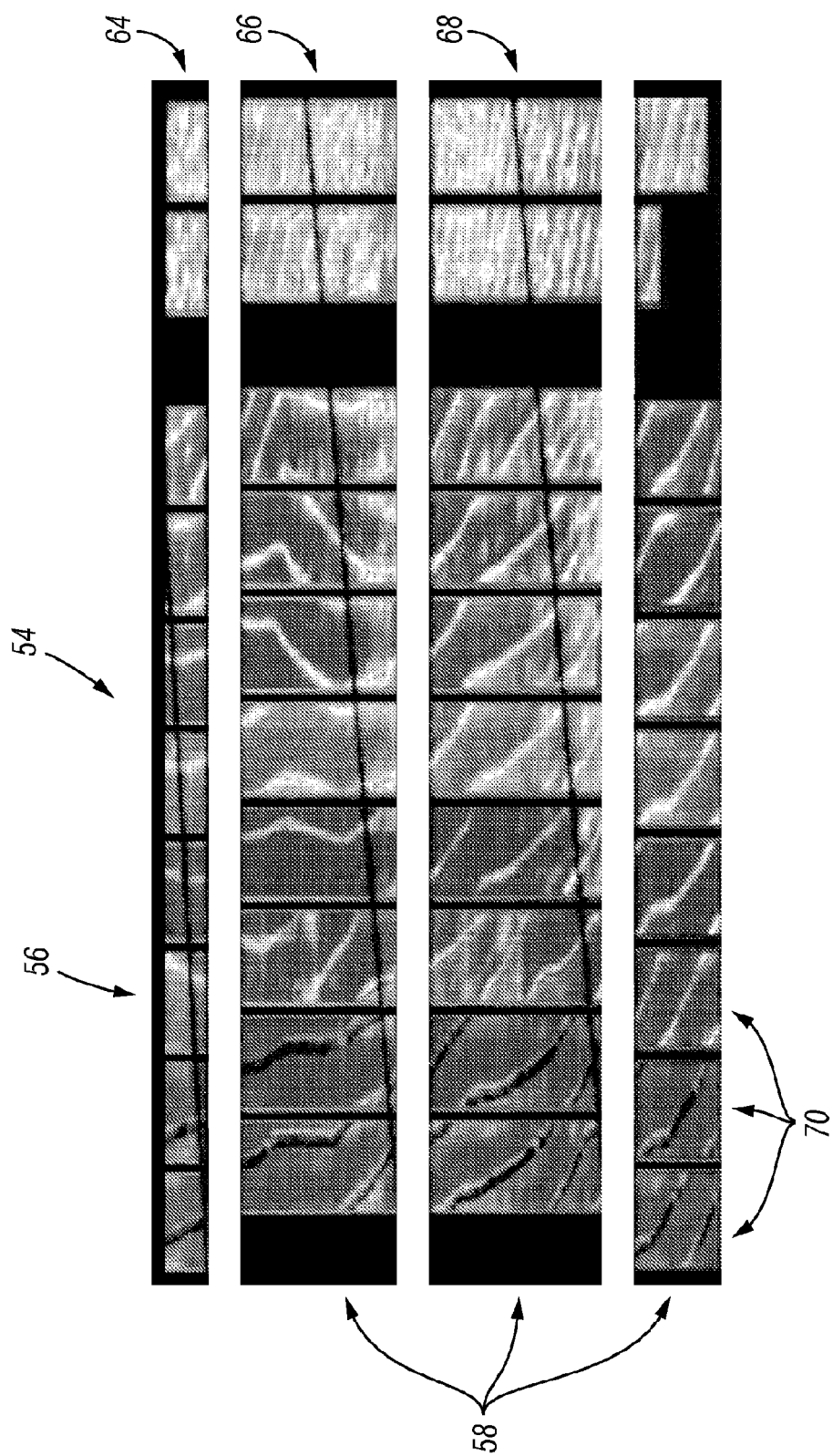
FIG. 7 is a graphical representation of data output by the monitoring system indicating another example of progressively changing conditions within a pipe, according to another embodiment of the disclosure.

In another example, the magnetic sensor system 24 and magnetic sensor 26 utilize a magnetic flux leakage signal indicative of a condition such as bias weld spiraling. The magnetic sensor 26 is able to detect bias weld spiraling in pipe 30 via changes to the magnetic flux leakage signal as the pipe 30 moves past magnetic sensor system 24, and/or vice versa. The data from magnetic sensor 26 may be output to graphical user interface 56, as illustrated in FIG. 7. In this particular example, the graphical user interface 56 illustrates three zones 64, 66 and 68 indicative of the progression of the condition in coiled tubing 42 over time, e.g. over a plurality of operations 70 utilizing the same coiled tubing 42. Again, data from magnetic sensor 26 establishes a signature indicative of changes in the bias weld spiraling. In the example illustrated in FIG. 7, the data indicates progressive damage to the coiled tubing 42 as the seam weld increasingly curls up during sequential coiled tubing operations.

However, the above-described examples of conditions detected and monitored are representative of a wide variety of conditions that can be detected and monitored in pipe 30 and/or internal component 34 via magnetic sensor 26 positioned externally of the pipe 30. The detection and monitoring may be accomplished by individual or plural magnetic sensors 26 positioned along the pipe exterior 40, and the sensor or sensors may be employed to output data related to various signatures indicative of specific conditions and conditional changes.

Additionally, the data may be output in many different forms. For example, the data may be output in graphical form, as raw data, as recommendations, as warnings, or as various combinations of these outputs. Additionally, the information may be output via graphical user interface 56 or via other suitable forms for a given monitoring operation. The output regarding condition signatures and changes in those signatures as the pipe is used from one operation to the next can be displayed locally and/or at remote locations. For example, the data may be relayed via the Internet or another communication system to remote centers for further observation, analysis, and/or determination of corrective actions. Examples of corrective actions include adjustment, repair, or replacement of the pipe 30 and/or internal component 34.

The magnetic sensor system 24 facilitates detection of potential problems by enabling monitoring of the pipe and/or internal component via an external sensor. The monitoring may be used in well related applications and non-well related applications. In well applications, the monitoring technique may be employed with many types of ferrous-based pipe, such as coiled tubing. The coiled tubing may be used and monitored repeatedly in successive intervention operations or other well servicing operations. The technique also may be used with other types of pipe by placing suitable tracers (such as by tagging the pipe with ferromagnetic materials or active magnetic sources as recited hereinabove) along the pipe and/or internal component to enable detection and monitoring by magnetic sensor 26.

Various systems and techniques also may be employed for causing the relative motion between the pipe 30 and the magnetic sensor system 24. For example, a variety of motive units may be used to move the pipe 30 linearly in a longitudinal direction through the magnetic sensor system 24. However, some applications may utilize movement of the magnetic sensor system 24 while the pipe 30 remains stationary or movement of both components to create the relative motion. In coiled tubing applications, the monitoring of specific conditions may be achieved while the coiled tubing is unspooled or spooled via coiled tubing reel 48.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for monitoring pipe, comprising:
    positioning a magnetic sensor system along an exterior of a coiled tubing, wherein positioning comprises positioning a magnetic flux leakage sensor along the exterior of the coiled tubing;
    causing relative movement between the coiled tubing and the magnetic sensor system when the coiled tubing is employed for a given operation;
    accumulating data from the magnetic sensor system during the given operation;
    repeating the positioning and causing of relative movement at a plurality of subsequent operations;
    accumulating data from the magnetic sensor system during the plurality of subsequent operations;
    using the accumulated data from the magnetic sensor system to measure and monitor changes in stretching of the coiled tubing during the plurality of subsequent operations; and
    using the magnetic sensor system to detect cable slack of a cable located within the coiled tubing.

2. The method as recited in claim 1, further comprising pumping fluid through an interior of the coiled tubing while using the magnetic sensor system to monitor changes in real time.

3. The method as recited in claim 1, wherein positioning comprises positioning the magnetic sensor system between a coiled tubing reel and a coiled tubing injector.

4. The method as recited in claim 3, wherein causing relative movement comprises operating the coiled tubing reel to spool the coiled tubing and thus move the coiled tubing past the magnetic sensor system.

5. The method as recited in claim 3, wherein causing relative movement comprises operating the coiled tubing reel to unspool the coiled tubing and thus move the coiled tubing past the magnetic sensor system.

6. The method as recited in claim 1, wherein repeating comprises employing the coiled tubing in a plurality of downhole operations.

7. The method as recited in claim 1, wherein repeating comprises employing the coiled tubing in a plurality of downhole intervention operations.

8. The method as recited in claim 1, wherein using comprises using the magnetic sensor system to monitor seam weld spiraling of the coiled tubing from one operation to the next.

9. The method as recited in claim 1, further comprising using the magnetic sensor system to detect abnormalities of a component within the coiled tubing.

10. A method, comprising:
    using a magnetic flux leakage sensor positioned along an exterior of coiled tubing to measure and monitor for a condition on or within the coiled tubing as the coiled tubing is moved longitudinally with respect to a wellbore for a given well operation;
    accumulating data from the magnetic flux leakage sensor while measuring and monitoring during the given well operation;
    repeating the measuring, monitoring and accumulating data for a plurality of subsequent well operations;
    comparing the accumulated data from the magnetic flux leakage sensor for the given well operation and the plurality of subsequent well operations to determine a progression of the condition, wherein the measured and monitored condition comprises coiled tubing stretching; and
    using the magnetic sensor system to detect cable slack of a cable located within the coiled tubing.

11. The method as recited in claim 10, wherein comparing the accumulated data further comprises determining the progression of coiled tubing bias weld spiraling.

12. The method as recited in claim 10, wherein the coiled tubing is unspooled into the wellbore and spooled out of the wellbore during each well operation and subsequent well operations.

* * * * *